(12) United States Patent
Gentz et al.

(10) Patent No.: US 11,779,704 B2
(45) Date of Patent: Oct. 10, 2023

(54) STATUS INDICATOR FOR DRUG DELIVERY SYSTEMS

(71) Applicant: Ypsomed AG, Burgdorf (CH)

(72) Inventors: Michael Gentz, Burgdorf (CH); Thomas Rufer, Ostermundigen (CH)

(73) Assignee: Ypsomed AG, Burgdorf (CH)

( * ) Notice: Subject to any disclaimer, the term of this patent is extended or adjusted under 35 U.S.C. 154(b) by 480 days.

(21) Appl. No.: 17/035,011

(22) Filed: Sep. 28, 2020

(65) Prior Publication Data

US 2021/0023299 A1 Jan. 28, 2021

Related U.S. Application Data

(63) Continuation of application No. PCT/IB2019/052427, filed on Mar. 26, 2019.

(30) Foreign Application Priority Data

Mar. 29, 2018 (EP) .................................... 18164906

(51) Int. Cl.
*A61M 5/172* (2006.01)
*G05B 11/01* (2006.01)
(Continued)

(52) U.S. Cl.
CPC ............. *A61M 5/172* (2013.01); *G05B 11/01* (2013.01); *G08B 5/38* (2013.01); *G08C 19/16* (2013.01);
(Continued)

(58) Field of Classification Search
CPC ......... A61M 5/172; G05B 11/01; G08B 5/38; G08C 19/16
(Continued)

(56) References Cited

U.S. PATENT DOCUMENTS 6,658,577 B2 * 12/2003 Huppi ................... G06F 1/1684
713/323
9,774,749 B1 * 9/2017 Skrainar ............ H04N 1/00076
(Continued)

FOREIGN PATENT DOCUMENTS

CN 101120618 A 2/2008
EP 3545991 A1 10/2019
(Continued)

OTHER PUBLICATIONS

International Preliminary Report on Patentability received for International Application No. PCT/IB2019/052427, dated Sep. 29, 2020, 6 pages.
(Continued)

*Primary Examiner* — Kerri L McNally
(74) *Attorney, Agent, or Firm* — Dorsey & Whitney LLP

(57) ABSTRACT

Electronic modules for attachment to a drug delivery device include delivery status sensing means (21, 22) for monitoring a delivery status of the device, a status indicator (25) with an indicator element controllable to indicate a delivery or module status, and a status indicator controller (23), which generates an indicator control signal on behalf of the status indicator element, which in turn produces a status signal. The indicator control signal has an amplitude varying monotonically in time between a minimum value and a maximum value in a first interval of a base cycle, and between the maximum value and the minimum value in a second interval of the base cycle. In at least one of the first and the second interval, the mean value of the indicator control signal is below the average of the maximum and the minimum values of the indicator control signal to realize increased energy savings.

20 Claims, 3 Drawing Sheets

(51) Int. Cl.
*G08B 5/38* (2006.01)
*G08C 19/16* (2006.01)
*A61M 5/142* (2006.01)

(52) U.S. Cl.
CPC ............ *A61M 2005/14208* (2013.01); *A61M 2205/273* (2013.01); *A61M 2205/583* (2013.01); *A61M 2205/587* (2013.01); *A61M 2205/8206* (2013.01)

(58) Field of Classification Search
USPC .................................................. 340/815.54
See application file for complete search history.

(56) References Cited

U.S. PATENT DOCUMENTS

| | | | |
|---|---|---|---|
| 2002/0178388 A1 | 11/2002 | Huppi et al. | |
| 2007/0046255 A1 | 3/2007 | Kim | |
| 2008/0278221 A1 | 11/2008 | Rowland | |
| 2010/0069830 A1* | 3/2010 | Grigorov | A61M 5/1456 604/67 |
| 2011/0270188 A1* | 11/2011 | Caffey | A61M 5/14593 604/151 |
| 2012/0089114 A1 | 4/2012 | Hemond et al. | |
| 2016/0047685 A1* | 2/2016 | Biei | G06V 30/413 250/227.11 |
| 2017/0368256 A1 | 12/2017 | Nessel et al. | |
| 2018/0043105 A1* | 2/2018 | Nazzaro | A61M 5/1684 |
| 2018/0064881 A1* | 3/2018 | Whalley | A61M 5/31541 |
| 2021/0008288 A1 | 1/2021 | Kappeler et al. | |
| 2021/0008294 A1 | 1/2021 | Gentz | |

FOREIGN PATENT DOCUMENTS

| | | |
|---|---|---|
| EP | 3545992 A1 | 10/2019 |
| EP | 3545993 A1 | 10/2019 |
| WO | 2004023637 A1 | 3/2004 |
| WO | 2008049609 A1 | 5/2008 |
| WO | 2011022850 A2 | 3/2011 |
| WO | 2016118736 A1 | 7/2016 |
| WO | 2016142727 A1 | 9/2016 |
| WO | 2017148857 A1 | 9/2017 |
| WO | 2018036938 A1 | 3/2018 |
| WO | 2018041798 A1 | 3/2018 |
| WO | 2018064784 A1 | 4/2018 |
| WO | 2019186381 A1 | 10/2019 |
| WO | 2019186412 A1 | 10/2019 |
| WO | 2019186413 A1 | 10/2019 |

OTHER PUBLICATIONS

International Preliminary Report on Patentability received for International Application No. PCT/IB2019/052470 dated Sep. 29, 2020, 9 pages.
International Preliminary Report on Patentability received for International Application No. PCT/IB2019/052471, dated Sep. 29, 2020, 9 pages.
English Translation of Chinese publication No. 101120618 A, provided by the European Patent Office with the issuance of the Extended European Search Report.
International Search Report and Written Opinion received for International Application No. PCT/IB2019/052470 dated Jun. 13, 2019, 13 pages.
International Search Report and Written Opinion received for International Application No. PCT/IB2019/052471, dated Jun. 13, 2019, 14 pages.
International Search Report and Written Opinion received for International Application No. PCT/IB2019/052427, dated Jun. 17, 2019, 10 pages.
Extended European Search Report issued in European Patent Application No. 18164896.5, dated Jul. 2, 2018, 8 pages.
Extended European Search Report received for European Application No. 18164906.2, dated Oct. 10, 2018, 6 pages.
Extended European Search Report received for European Application No. 18164883.3, dated Nov. 15, 2018, 8 pages.

* cited by examiner

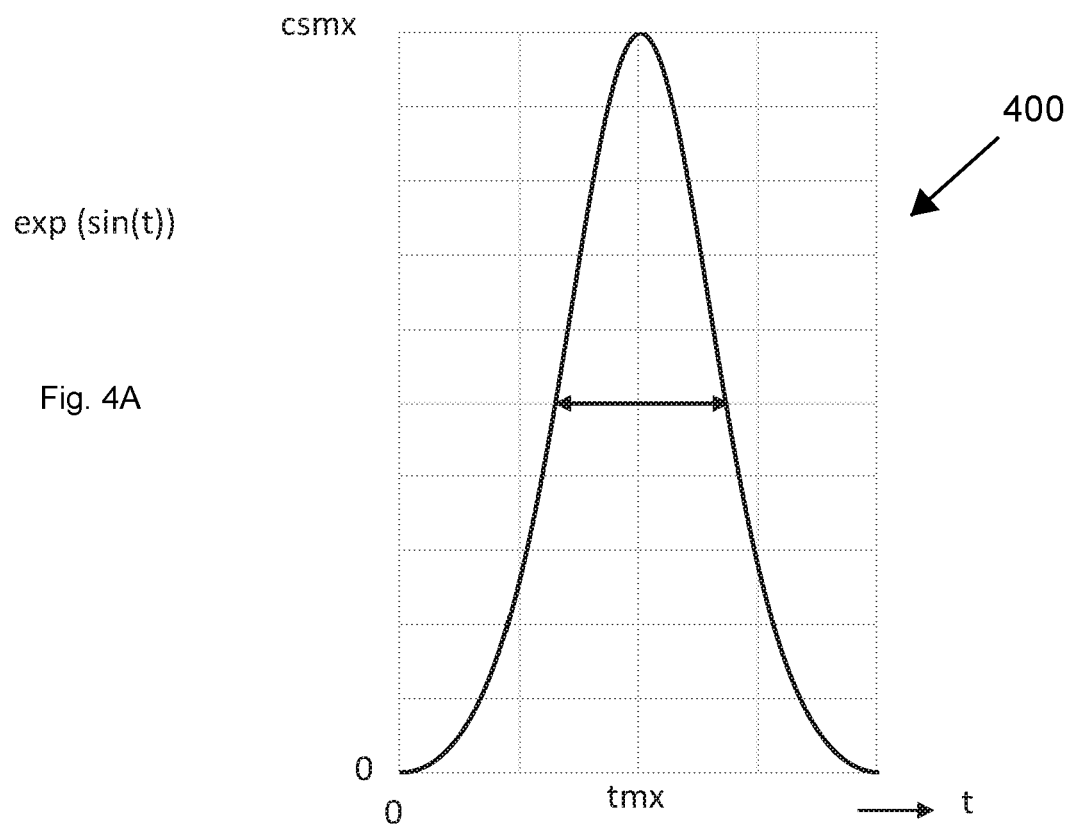
Fig. 4A  exp(sin(t))
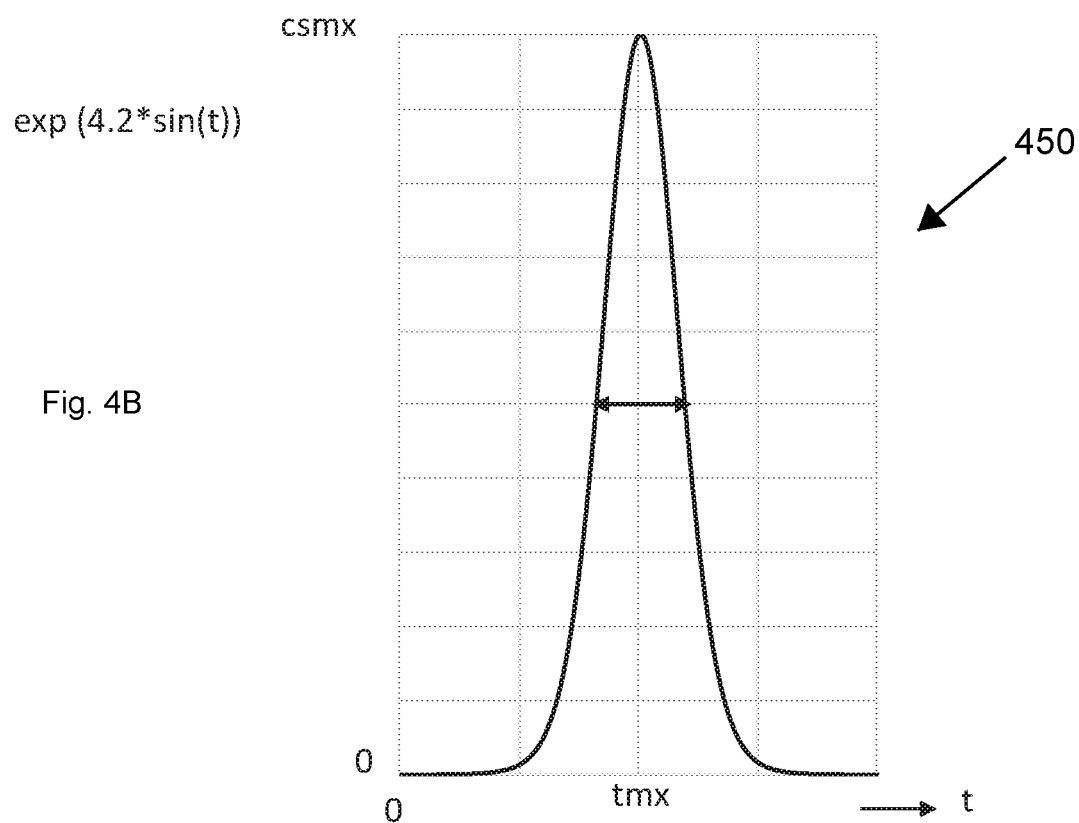
Fig. 4B  exp(4.2*sin(t))

STATUS INDICATOR FOR DRUG DELIVERY SYSTEMS

CROSS REFERENCE TO RELATED APPLICATIONS

This application is a continuation of International Patent Application No. PCT/IB2019/052427, filed Mar. 26, 2019, entitled "STATUS INDICATOR FOR DRUG DELIVERY SYSTEMS," and which claims priority to European Patent Application No. 18164906.2, filed Mar. 29, 2018, entitled "STATUS INDICATOR FOR DRUG DELIVERY SYSTEMS", each of which is incorporated by reference herein, in their entireties and for all purposes.

TECHNICAL FIELD

Implementations relate to drug delivery systems for delivering, administering, injecting, infusing or dispensing liquids comprising a drug, medicament, or active ingredient that includes an electronic module attachable to a disposable injection device.

BACKGROUND

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time. Disposable delivery devices are adapted to deliver a drug from a container such as a pre-filed syringe that is not intended to be replaced or refilled by the patient. Reusable, semi-reusable, or hybrid delivery devices have at least a container and possibly also a container holder that may be replaced by the patient, or a cartridge that may be refilled, while some components of the device may be reused with the replaced or refilled drug container. By way of example, diabetes may be treated by administration of insulin by the patients themselves with the help of multi-variable-dose insulin injection pens or infusion pumps.

Fixed dose disposable injection devices include single-dose injection devices such as auto injectors or patch injectors as well as multi-dose injection devices such as fixed dose injectors. Auto-injectors automatically deliver a fixed dose of liquid drug from a pre-filled syringe by means of a pre-strained injection spring biasing a piston rod and shifting a piston in a syringe barrel. Patch injectors or ready-to-use pre-filled wearable bolus injectors are attached or adhered to the skin of the patient in view of a single dose injection taking between thirty seconds and several minutes. Fixed-dose injectors have a single, non-variable dosage volume, or eventually provide a limited number of fixed, non-variable injection dosage volumes for the user to choose from.

Disposable delivery devices may be complemented by a monitoring or control unit being part of a reusable electronic module or auxiliary device adapted to be successively attached to the device housings of plurality of disposable delivery devices. The monitoring unit serves to monitor the delivery process, in order to proactively prevent or retroactively recognize false handling of the device and to keep track of the doses already applied. In addition to generating data related to an instantaneous status, condition, or use of the delivery device, information on the drug type, cartridge batch, and/or expiration date may be evaluated by the monitoring unit. To that end, the electronic module comprises a delivery status sensing unit for tracking a progress of a medication event performed by means of the delivery device and/or for reading drug information that is stored on a machine-readable tag mounted to the device housing. The module may further comprise a status indicator for signaling status and drug information to a user, and a wireless communication unit for communicating status and drug information to a nearby mobile device or medical gateway. All of these units are supplied with power from an energy storing unit of the electronic module. An exemplary electronic module with a sensing unit capable of discerning various operational states of a disposable auto-injector is disclosed in PCT Publication No. WO 2018/064784 A1 (PCT/CH2017/050004).

A monitoring or control unit with the aforementioned sensor, indicator and communication functionalities may be part of a reusable electronic delivery device and, as such, be integrated into a device housing of the delivery device comprising the reusable components. In this case, the electronic delivery device may be a reusable injection pen with a monitoring unit and a manually powered delivery drive requiring a user to manually provide the energy to move the piston or to charge a drive spring. The electronic delivery device may also be a reusable infusion pump with a monitoring unit and with a motor driving the piston automatically. All sensing, reading, evaluating, indicating, data processing, and communicating facilities of the monitoring module are powered by an energy storing unit of the reusable delivery device.

Well-known, energy-saving power management strategies in battery powered mobile devices include activating power consuming components including sensors, processors, and communication units non-permanently in a selective manner, specifically only for a minimum period of time corresponding to a duty cycle, e.g., when the device is active. For instance, a Bluetooth communication unit of a mobile device may be activated or powered only for a few milliseconds every few seconds without impairing the communication sendees. On the other hand, light guides illuminated by LEDs and terminating on the device housing are being frequently used as status indicators in mobile devices, such that the illuminating LEDs have to be active for extended periods of time. Accordingly, LEDs or other optical indicators, as well as acoustic or tactile human machine interface (HMI) elements including buzzers or vibrating elements, may account for a considerable share in total power consumption. Operating LEDs in pulse-type modes with prolonged idle dark times is not practical for indicating a regular or active device operation mode, and blinking modes with rapid on/off may preferably be reserved for alarm signaling. Reducing the amplitude of the LED signal is another option for saving battery power, but may not be practical in bright daylight.

U.S. Pat. No. 6,658,577 contends that an LED blinking effect resulting from periodic, i.e., once per second, identical electrical energy pulses does not provide a pattern that is visually appealing to the observer, while a gradually varying intensity of the electrical pulses in combination with a quiet (e.g., non-energized or zero intensity) period mimics the rhythm of breathing which is psychologically appealing and provides a preferred visual experience for users. In U.S. Pat. No. 6,658,577, the energy consumption of a sleep-mode status indicator for laptop computers is a minor issue, and in any case power savings are primarily being realized by a quiet period of variable duration rather than by the a further optimized shape of the LED signal.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

SUMMARY

It is an objective of the present disclosure to indicate a status of a drug delivery device with a user-appealing, breathing type signal and reduced power consumption by providing an electronic module and a drug delivery device according to the present disclosure.

According to implementations, an electronic module is provided for removable attachment to a device housing of a disposable drug delivery device holding a container with a liquid drug. The electronic module includes delivery status sensing means for monitoring a delivery status of the delivery device, a status indicator with an indicator element such as a Light Emitting Diode (LED) controllable or controlled to indicate a delivery or module status, and a status indicator controller. The status indicator controller is adapted or configured to process an indicator control signal on behalf of the status indicator element, which in turn defines or produces a user-perceivable status signal or output of the status indicator. The indicator control signal has an amplitude varying monotonically in time between a minimum value and a maximum value in a first interval of a base cycle, and between the maximum value and the minimum value in a second interval of the base cycle. In at least one of the first and the second interval, the mean value of the indicator control signal is below the average of the maximum and the minimum values of the indicator control signal, or equivalently, the integral of the indicator control signal curve is less than the product of said average and the interval length. Specifically, if the minimum value is equal to zero, the mean value is less than 0.5 of the maximum value, and preferably less than 0.375, and most preferably less than 0.25 thereof. Advantageously, this criteria applies to each of the first and the second interval individually.

An alternative criteria for the indicator control signal requires that the duration of the indicator control signal with a value above the average of the maximum and the minimum value is shorter than the duration of the indicator control signal with a value below the average. In other words, the time-wise fraction or share of the indicator control signal of the first or second interval with a value above average is less than 0.5, and preferably less than 0.375, and most preferably less than 0.25.

The indicator control signal is to be understood as a low frequency signal that describes or defines the shape of an intended user-perceivable status signal irrespective of any modulated high frequency carrier signals or pulses, which are not individually perceptible by a user. In other words the indicator control signal may be a target, duty-cycle, or modulating function chosen in view of the intended status signal and provided to a controller modulator. The indicator control signal may be an envelope or low-pass filter output of a controller modulator output signal generated on the basis of such target function, for instance by means of pulse width modulation, and intended to be fed to the indicator element. The indicator control signal of the status indicator controller may also represent a continuously varying voltage applied to the status indicator or a continuously varying current supplied to the status indicator.

The first and the second interval are defined as including only monotonically or continuously increasing, or monotonically or continuously decreasing, indicator control signal values that lead to a user-perceptible gradual change in the status signal. Such a gradual change is distinctly slower than a blinking or otherwise discontinuous status signal change, and may take at least 0.2, preferably at least 0.5 seconds to complete. This definition of the intervals explicitly excludes any leading or trailing intervals at a constant control signal value. Leading or trailing intervals may well be present in a repeating cycle, such as a quiet period at zero intensity or a minimum signal period at less than a few percent of the maximum intensity providing a faint, glow-type visual signal. Any interval or period with such a non-varying control signal provided between the end of a second interval and the start of a next first interval may be used to adapt the frequency of the signal maxima, but is disregarded for the purpose of the present invention. Any potential user-perceptible intermediate plateau results in a split of the first or second interval into two or more subintervals to which the proposed criteria do apply individually.

The status indicator includes a specific indicator element such as an LED and/or buzzer that will produce an indicator output signal with a user-perceivable brightness, volume, intensity, power, and/or the like. As the brightness of an LED varies proportional to the LED current, a reduced mean control current value implies a reduction in time-integrated current or charge consumed by the LED and previously stored at an energy storing unit. Other quantities for characterizing the indicator output may vary according to an output function distinct or separate from the indicator control signal, and depend on the specifics of the indicator element. For instance, in case of an indicator element with a constant electrical resistance the dissipated power will vary according to the applied voltage squared, such that a triangular or a sinusoidal indicator control signal voltage gives rise to a power output function for which the integral indicative of the energy dissipated is exactly one third or about 38%, respectively, of the value corresponding to a continuous maximum power output. For indicator elements with any current-voltage characteristics, indicator control signals according to the invention, however, will lead to an even more concentrated power output function with a mean value that is further reduced as compared to the triangular or sinusoidal control signal. Accordingly, increased energy savings are realized and current consumption is reduced, which benefits the dimensioning of the energy storing unit, specifically the capacity requirements of a battery.

The invention is based on the insight that a regular user experiences a kind of saturation effect close to the nominal maximum intensity of a repeating LED indicator signal, and may hardly distinguish any details in the brighter part of the signal. In particular, a smooth approach to the maximum intensity may not be distinguished from a signal peak with a discontinuous derivative. With the overall impression of natural breathing being predominantly determined by the signal shape at lower to medium intensity, the invention proposes to shorten or reduce the fraction of a resulting status output signal at higher intensities and to expand the share at lower intensities. Correspondingly, the integrated intensity of the output signal as being proportional to or at least indicative of the energy consumed per cycle may be reduced as compared to an indicator control signal with a mean value equal to half the maximum value, such as triangular or sinusoidal duty cycle functions.

Status sensors included in the monitoring modules or units may be of any type suitable for detecting a present state of the delivery device, or an operation or process being executed by the delivery device, or a user activity performed on the delivery device. The sensors may include any of optical, electrical (contact, magnetic, inductive, RFID), force, pressure, and temperature sensors, as well as accelerometers capable of detecting the delivery device being seized, or even a single or multiple tapping movement of the user. Accordingly, discernable device statuses include any of the device being held or tapped, a drug temperature being equilibrated prior to delivery, a device cap being removed, a communication interface being activated, an electronic module being attached, a device tag being read, delivery device placed adjacent to injection site, drug delivery started, drug delivery ended, holding time ongoing, delivery device removed from injection site, needle shield locked, electronic module removed from delivery device, and so on.

In some embodiments the electronic module is adapted or configured to process an indicator control signal of which the value increases exponentially in time during the first interval, and/or decreases exponentially during the second interval. Specifically, this definition encompasses terms with exponentials of a function of the time variable t, i.e. $y(t)=\exp(f(t))$. Alternative arithmetic definitions of the indicator control signal shape include power functions with terms proportional to the time variable t raised to a power in excess of one, i.e. $y(t)=t^a$ with $a>1$.

In further variants, the indicator control signal presents or exhibits, at the end of the first interval, a discontinuous derivative at the maximum value; the decreasing signal of the second interval is symmetric to the increasing signal of the first interval; the second interval immediately follows the first interval thus excluding a plateau with maximum control signal value in-between the two intervals; and/or in a repetition of base cycles, no quiet period is present between the end of a second interval and the start of an ensuing first interval.

In a further embodiment, the electronic module comprises an ambient light sensor producing a sensor output indicative of an ambient light intensity, and the indicator control signal is adjusted according to the sensor output. Specifically, an adjusted indicator control signal with adapted control parameters produces a further narrowed light pulse when more ambient light is competing with the signal of the status indicator, and at the same time increases the amplitude such that consumption of power from the energy storing unit is about unchanged. At lower ambient light intensity, a lower maximum amplitude may be chosen together with a wider, i.e., less concentrated control signal shape which in combination still contributes to saving energy of the energy storing unit. In parallel, the minimum control signal value and/or a quiet period between successive cycles may also be adapted in dependence on said sensor output. In an analogous manner, a background noise level may be measured and compensated in the case of an acoustical status indicator.

In other preferred embodiments, the electronic module includes a battery that is mounted or embedded in the module in a manner which prevents non-destructive replacement and devoid of any means for recharging, as an energy storing unit for sourcing the status sensing means and the status indicator. The non-replaceable battery may also power a communication unit of the electronic module for data exchange with a mobile device. The electronic module may be attached to a disposable injection device, and an injection status may be determined by the status sensing means of the electronic module.

According to implementations, a mobile and reusable drug delivery device is provided with a replaceable container for a liquid drug, and with an electronic monitoring unit including a delivery status sensing means for monitoring a delivery status of the delivery device. The delivery device includes a status indicator controllable to indicate a delivery status by repeated emission of a status signal. The delivery device includes a status indicator controller adapted to process an indicator control signal for controlling the status signal of the status indicator, the indicator control signal varying monotonically between a minimum and a maximum value in a first interval and between the maximum and the minimum value in a second interval, wherein in the first or in the second interval, the mean value of the indicator control signal is below the average of the maximum and the minimum values of the indicator control signal. The invention may alternatively be used with reusable drug delivery devices that include a monitoring unit with the aforementioned sensing, reading, evaluating, data processing, and communication functionalities integrated into a device housing of the delivery device. The delivery device includes a non-replaceable, non-rechargeable energy storing unit such as a battery for autonomously powering both the monitoring unit and the status indicator. This battery may be distinct or separate from a source of energy provided for moving a piston in order to deliver the liquid drug.

BRIEF DESCRIPTION OF THE DRAWINGS

The subject matter of the invention will be explained in more detail in the following text with reference to preferred exemplary embodiments which are illustrated in the attached drawings, in which:

FIGS. 3A-3B and FIGS. 4A-4B depict various indicator control signal shapes.

The reference symbols used in the drawings, and their primary meanings, are listed in summary form in the list of designations. In principle, identical parts are provided with the same reference symbols in the figures.

DETAILED DESCRIPTION OF PREFERRED EMBODIMENTS

Figure 1:
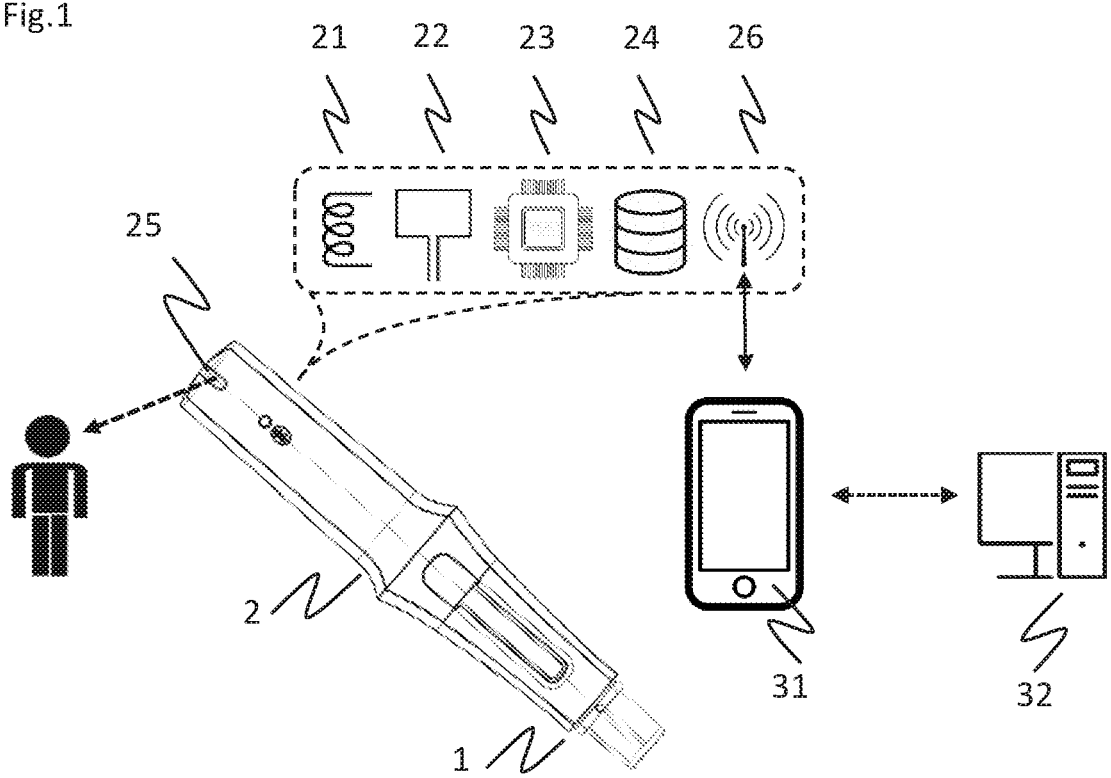
FIG. 1 depicts a medical monitoring system with an auto-injector according to the present disclosure.

FIG. 1 depicts an implementation of a medical monitoring system, comprising an auto-injector as an exemplary disposable injection device 1, an electronic module 2 releasably attached to a device housing of the injection device, and a mobile device 31 such as a smartphone or tablet device running a dedicated application program; or a laptop computer configured accordingly. The mobile device 31 is communicatively connected via a data communication network, e.g., the Internet, to a remote server, cloud based computing facility, or expert system 32. The electronic module 2 comprises status sensing means or a status sensor including an electrical or mechanical feedback sensor 21 and a tag reader 22 for reading drug information from a tag or label mounted to the device housing. The electronic module 2 further comprises a status indicator controller 23 for generating an indicator control signal on behalf of a status indicator 25. The latter includes an LED or any other type of HMI element for providing visual, acoustic, or tactile feedback about an injection status such as a progress of an ongoing injection process, based on the indicator control signal. A memory or data storage unit 24 is adapted to store status or delivery information. The electronic module 2 also comprises a communication unit 26 for wireless transmission of an injection status or drug status to the mobile device 31 via Bluetooth Low Energy (BTLE) or equivalent short or near range wireless communication technology. The electronic module 2 has a rear, or proximal, part where some or all electronic components as described are located.

Included in a module housing of the electronic module 2 is a lock/release mechanism to secure the attachment of the electronic module 2 to the injection device in order to protect against unintended detachment, for instance during removal of a needle protective cap from the auto-injector. The auto-injector is configured for automatically delivering a fixed dose of liquid drug from a pre-filled syringe by means of a pre-strained injection spring provided for biasing a piston rod and shifting a piston arranged in the syringe. The auto-injector comprises a needle protective sleeve, or cover sleeve, for protecting a needle of the syringe after removal from the injection site. Upon removal of the auto-injector from the injection site the needle protective sleeve is biased to a needle protecting position by a cover sleeve spring, and locked in this position by a locking means generating a locking sound. Start and end of a substance delivery as well as injection device removal from the patient may be detected by the injection status sensing means and may be combined to obtain a characterization of the ongoing injection process or medication event, in order to track whether an injection event has occurred according to the medication schedule, but also whether that injection was successfully completed or not. The injection status sensing means may include an electrical sensor such as a contact-free inductive or capacitive sensor. An exemplary inductive sensor may detect initial, intermediate, and final values of, and/or corresponding changes or differences in, a static or alternating magnetic field or flux depending on a position or displacement of a magnetic or electrically conductive device component.

The wireless communication unit 26 is connected to the memory or data storage unit 24 and/or to a processing unit, and adapted to wirelessly communicate, specifically upload, injection information retrieved from the storage or processing unit 24 to a nearby mobile device or dedicated medical gateway. The injection information may include a time stamp indicative of a time of a medication event as well as the expelled dose or other drug information read from a tag or label mounted to the device housing. The injection information may be transmitted instantaneously, or stored in the memory unit 24 connected to the processing unit, for later upload or batch transfer. The injection information may, in addition or alternatively, include a quality measure of an injection process, such as a binary flag indicating that a minimum holding time requirement has been complied with.

Figure 2:
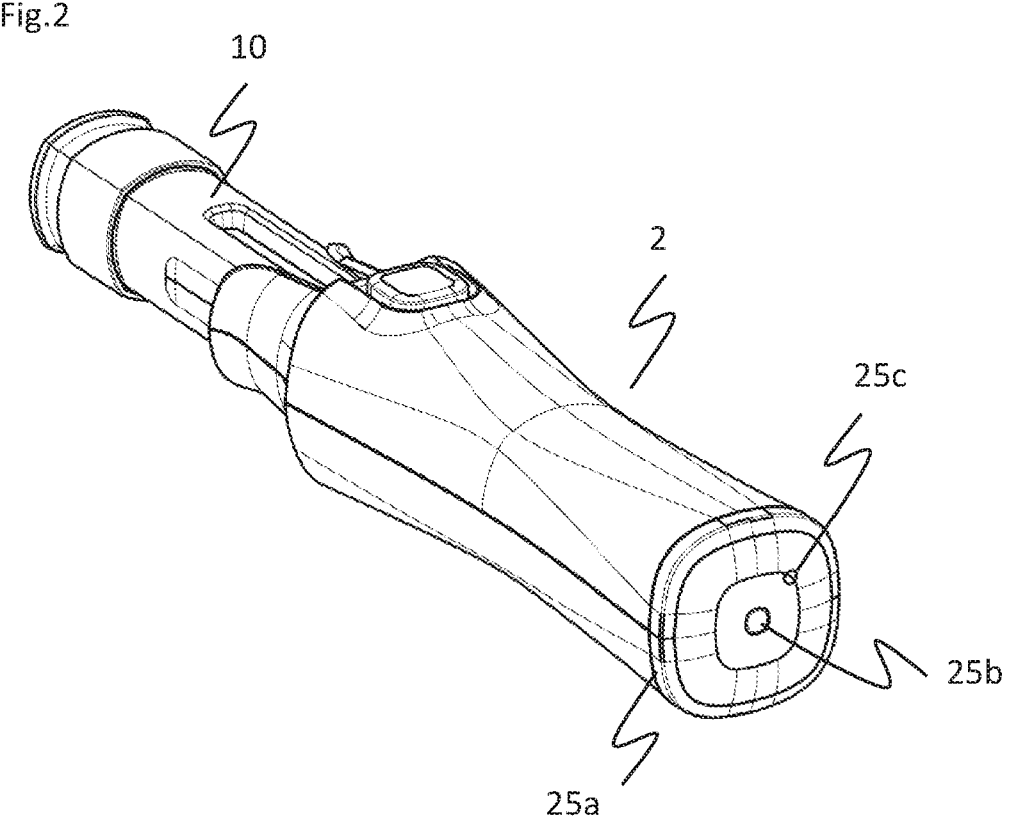
FIG. 2 depicts an alternative electronic module.

FIG. 2 discloses a rear view of another embodiment of an electronic module 2 mounted to the housing 10 of an injection device. As an alternative to the status indicator 25 of FIG. 1, the module 2 of FIG. 2 includes a spot-shaped or circular-shaped status indicator element 25b being located on a rear or proximal end surface of the module 2, and a ring-shaped status indicator element 25a being located around the proximal edge of the electronic module 2. Due to its peripheral location, the ring-shaped status indicator element 25a is visible even when the module is held by a user, and due to its circumferential shape, may be observed from all sides and under different angles, in particular during delivery when the injection device has been placed adjacent to an injection site. A Bluetooth Low Energy (BLE) connect status indicator element 25c is further provided to signal a connected status of the communication unit 26.

Providing two distinct or separate status indicators 25a, 25b allows to further refine the visual messages that the electronic module is to convey to a user. In addition to adapting an altering pattern of a single indicator as described below, the interplay between spot-shaped and ring-shaped status indicators 25b, 25a, respectively, facilitates optimized energy management and extended battery lifetime. For instance, exclusive use of the spot-shaped status indicator 25b with a signal according to the implementations provided herein may indicate a wait-mode, e.g., while a drug substance is warmed up for a few minutes to reach delivery temperature. As the illuminating LED requires less power for a given intensity, the smaller surface of the spot-shaped indicator 25b promotes use thereof for status indication during extended intervals A timer or an acceleration sensor detecting user activity may subsequently cause the mode to switch from wait-mode to activated, and to switch visual interface from the spot-shaped 25b to the ring-shaped indicator 25a.

Figure 3A:
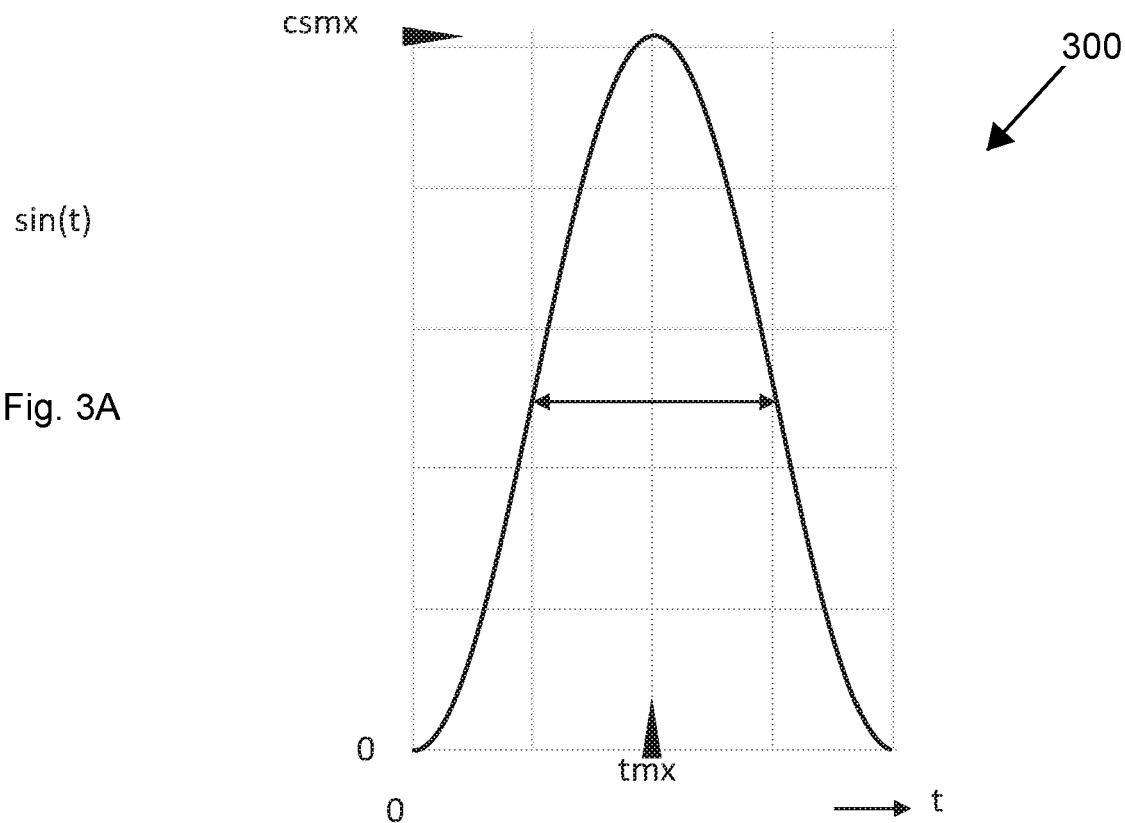
Figure 3B:
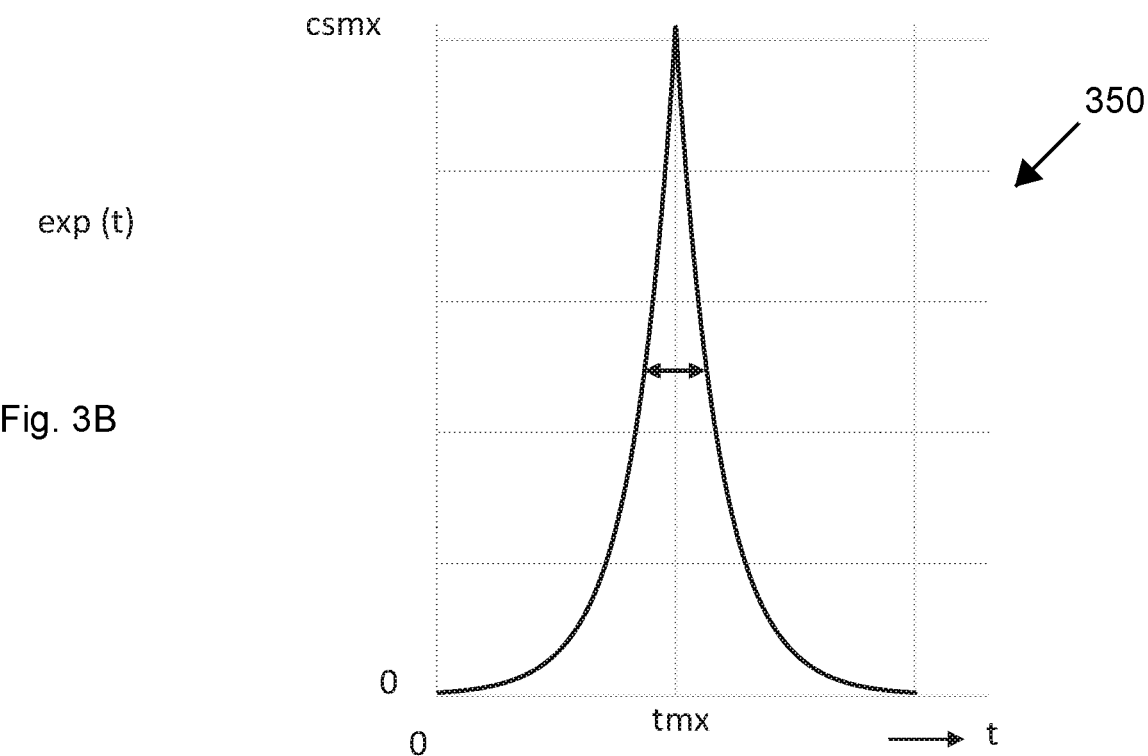

FIGS. 3A and 3B depict two properly scaled indicator control signal curves over a single base cycle consisting of a first and a second interval and having a total duration 2*tmx of generally between one and five seconds. The graph 300 of FIG. 3A shows a sinusoidal or biased-sinusoidal indicator control signal curve and the graph 350 of FIG. 3B shows an exponential indicator control signal curve described in the first interval as:

$$y(t) = \frac{e^{a*t} - 1}{e^{a*tmx} - 1} * csmx$$

Both curves are symmetric about the time tmx of the maximum value csmx of the indicator control signal. For the sinusoidal signal (FIG. 3A) the integral of the curve depicted is exactly one half of the area of the chart, the latter being given by 2*tmx*csmx, and the mean indicator control signal value likewise is one half of the maximum indicator control signal value max. For the exponential signal (FIG. 3B), with exemplary parameter values a*tmx of 1.5 and 3.6, the integral and the mean indicator control signal value amount to 0.38 and 0.25, respectively, of the chart area or of the maximum indicator control signal value csmx, respectively. The curve depicted in FIG. 3B may be based on a further increased parameter a*tmx of 5.2 which decreases the integral of the curve and the mean indicator control signal value amount to 0.19 of the chart area or of the maximum indicator control signal value csmx, respectively. For the sinusoidal signal the width of the control signal curve at a signal value equal to half of the maximum indicator control signal value csmx is exactly equal to one half of the base cycle, whereas for the exponential signal, this width is much lower, as indicated by the two horizontal arrows. In addition, for the exponential signal the first derivative is discontinuous both at t=tmx and maximum indicator control signal csmx, as well as at t=0, t=2*tmx and minimum indicator control signal.

FIGS. 4A and 4B depict graphs 400, 450, respectively, of two properly scaled indicator control signal curves over a single base cycle consisting of a first and a second interval and having a total duration of 2*tmx. Both curves are symmetric about the time tmx of the maximum value csmx of the indicator control signal, and are defined in the first interval as $$y(t) = \frac{e^{a*sin(\pi(\frac{t}{tmx}-\frac{1}{2}))} - e^{-a}}{e^a - a^{-a}} * csmx$$

For a parameter value of a=1 (FIG. 4A), the integral and the mean indicator control signal value amount to 0.38 of the chart area or of the maximum indicator control signal value csmx, respectively, with a fraction above average of 0.35. For a parameter value of a=3, the mean value decreases to 0.24. For a parameter value of a=4.2 (FIG. 4B), the integral and the mean indicator control signal value further reduce to 0.2 of the chart area or of the maximum indicator control signal value csmx, respectively, with a share of the signal curve with a value above the average of the minimum and maximum of 0.18.

The status indicator controller may prepare a controller modulator output signal as a series of Pulse Width Modulated (PWM) pulses occurring at a frequency ranging from 100 Hz to 500 kHz, with each pulse in the series having an identical peak current level corresponding to a maximum LED current. The electrical pulses include pulse widths that vary in accordance with a duty cycle or target function indicating the percentage of a base period that an electrical pulse is to stay at its peak current level. The duty cycle function representing the control signal shape thus determines the length of the individual pulses. For instance, a maximum pulse width corresponds to the entire base period being at maximum current, while a 20% duty cycle value corresponds to one fifth of the base interval being in on state. The base period in turn corresponds to the modulation frequency chosen, e.g., to 5 ms for an exemplary modulation frequency of 200 Hz.

Energy management becomes vital if an intended lifetime of an electronic module or of a delivery device equipped with a monitoring unit is to be provided without undue investments in battery size or quality, specifically when sourcing from energy storing units that are not intended to be replaced or recharged after completion of assembly. Following initial installation and activation, the electronic module or the delivery device may be turned off or at least put into a sleep mode during module or device idle periods of up to a few days or even weeks between successive delivery events. However, a turned-off module or device requires a mechanical switch to re-power a main processing unit prior to a next injection event. In the case of an electronic module, this switch may be actuated by the attachment of the electronic module to the delivery device, or by a cap of the injection device being removed from contact with the attached electronic module. A module or device in sleep mode with some residual functionality still being available requires an electronic switch, an acceleration sensor capturing a user-induced movement of the device, or an RFID tag receiving a user-induced RFID pulse as a trigger to re-power a main processing unit prior to a next injection event.

The status indicator of the electronic module or of the delivery device comprises a visual, audible and/or tactile status indicator element as a human interfacing means. The indicator element may include a single multicolor LED or a loudspeaker for generating language-independent sounds or simple melodies. The status indicator may explicitly exclude any advanced human-machine interfacing (HMI) capability. In particular, the status indicator may be devoid of a display, screen, or projector for visually transmitting readable instructions, and likewise exclude an artificial speech assistant for reading out loud the instructions. Such advanced HMI functionality including elaborate graphic display and speech output capabilities are preferably being provided by a mobile device communicatively connected to the electronic module or delivery device. To that end, the electronic module or the delivery device may comprise a communication unit to transmit the status information to a mobile device such as a smartphone or tablet device running a dedicated application program, or a laptop computer configured accordingly. Communication to the mobile device may preferably take place via Bluetooth Low Energy (BLE) or equivalent short or near range wireless communication technology.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

Injection device
10 Device housing
2 Electronic module
21 Inductive or feedback sensor
22 Tag reader
23 Status indicator controller
24 Memory or data storage unit
25 Status indicator
26 Communication unit
31 Mobile device
32 Remote server
300, 350, 400, 450 graphs

What is claimed is:

1. An electronic module for removable attachment to a device housing of a disposable delivery device holding a container with a liquid drug, the electronic module comprising:
a delivery status sensor configured to monitor a delivery status;
a status indicator for indicating a status; and
a status indicator controller, wherein an indicator control signal of the status indicator controller varies monotonically between a minimum value and a maximum value in a first interval and between the maximum value and the minimum value in a second interval, and wherein in the first interval or in the second interval, a mean value of the indicator control signal is below an average of the maximum value and the minimum value of the indicator control signal.

2. The electronic module of claim 1, wherein the indicator control signal of the status indicator controller increases exponentially between the minimum value and the maximum value during the first interval, or decreases exponentially between the maximum value and the minimum value during the second interval.

3. The electronic module of claim 1, wherein the indicator control signal exhibits a discontinuous derivative at the maximum value.

4. The electronic module of claim 1, wherein the indicator control signal of the second interval is symmetric to the indicator control signal of the first interval.

5. The electronic module of claim 1, wherein the indicator control signal includes a repetition of cycles comprising the first interval and the second interval, and wherein the second interval immediately follows the first interval.

6. The electronic module of claim 1, wherein the indicator control signal includes a repetition of cycles comprising the first interval and the second interval, and wherein the first interval immediately follows the second interval of a preceding cycle.

7. The electronic module of claim 1, wherein the electronic module comprises an ambient light sensor, and wherein the status indicator controller is adapted to adjust the indicator control signal according to a sensor output of the ambient light sensor.

8. The electronic module of claim 1, wherein the electronic module comprises a non-rechargeable, non-replaceable battery for powering the status sensor and the status indicator.

9. The electronic module of claim 1, wherein the status indicator controller is adapted to select an indicator control signal indicative of an injection status of a disposable injection device to which the electronic module is attached.

10. A drug delivery device, comprising:
a replaceable container for a liquid drug;
an electronic monitoring unit comprising a delivery status sensing means for monitoring a delivery status;
a status indicator for indicating a status; and
a status indicator controller, wherein an indicator control signal of the status indicator controller varies monotonically between a minimum value and a maximum value in a first interval and between the maximum value and the minimum value in a second interval, and wherein in the first or in the second interval, the mean value of the indicator control signal is below the average of the maximum and the minimum values of the indicator control signal.

11. The drug delivery device of claim 10, wherein the drug delivery device comprises a non-rechargeable, non-replaceable battery for powering the status sensing means and the status indicator.

12. The drug delivery device of claim 10, wherein the status indicator controller is adapted to process, during the first interval, an indicator control signal increasing exponentially between the minimum value and the maximum value, or to process, during the second interval, an indicator control signal decreasing exponentially between the maximum value and the minimum value.

13. The drug delivery device of claim 10, wherein the status indicator controller is adapted to process an indicator control signal including a repetition of base cycles comprising the first interval and the second interval, wherein the second interval immediately follows the first interval of a same base cycle, and wherein the first interval of a next base cycle immediately follows the second interval of a preceding base cycle.

14. The drug delivery device of claim 10, wherein the drug delivery device comprises an ambient light sensor, and wherein the status indicator controller is adapted to adjust the indicator control signal according to a sensor output of the ambient light sensor.

15. The drug delivery device of claim 10, wherein the indicator control signal exhibits a discontinuous derivative at the maximum value.

16. The drug delivery device of claim 10, wherein the indicator control signal of the second interval is symmetric to the indicator control signal of the first interval.

17. The drug delivery device of claim 10, wherein the indicator control signal includes a repetition of cycles comprising the first interval and the second interval, and wherein the second interval immediately follows the first interval.

18. The drug delivery device of claim 10, wherein the indicator control signal includes a repetition of cycles comprising the first interval and the second interval, and wherein the first interval immediately follows the second interval of a preceding cycle.

19. The drug delivery device of claim 10, wherein the status indicator controller is adapted to select an indicator control signal indicative of an injection status of the device.

20. The drug delivery device of claim 10, wherein the status indicator controller prepares a controller modulator output signal as a series of Pulse Width Modulated (PWM) pulses.

* * * * *